(12) United States Patent
Yuds et al.

(10) Patent No.: US 11,971,330 B2
(45) Date of Patent: Apr. 30, 2024

(54) LEAK DETECTOR ON MOVABLE MEDICAL DEVICE

(71) Applicant: Fresenius Medical Care Holdings, Inc., Waltham, MA (US)

(72) Inventors: David Yuds, Hudson, NH (US); Colin Weaver, Pleasanton, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 150 days.

(21) Appl. No.: 17/533,476

(22) Filed: Nov. 23, 2021

(65) Prior Publication Data
US 2023/0160775 A1    May 25, 2023

(51) Int. Cl.
*A61M 1/28* (2006.01)
*B60B 19/00* (2006.01)
*G01M 3/40* (2006.01)

(52) U.S. Cl.
CPC .............. *G01M 3/40* (2013.01); *A61M 1/282* (2014.02); *B60B 19/00* (2013.01); *A61M 2205/15* (2013.01); *A61M 2205/18* (2013.01); *A61M 2205/3327* (2013.01); *A61M 2205/3334* (2013.01); *A61M 2205/3553* (2013.01); *A61M 2205/3584* (2013.01)

(58) Field of Classification Search
CPC ..... A61M 2205/15; A61M 1/28; A61B 50/13; G01M 3/40; Y10T 137/5762; A47L 15/4212; G08B 21/20
See application file for complete search history.

(56) References Cited

U.S. PATENT DOCUMENTS

| 4,934,022 A | 6/1990 | Lissner |
| 5,184,373 A | 2/1993 | Lange |
| 9,610,931 B2 | 4/2017 | O'Meachair et al. |
| 9,782,302 B2 | 10/2017 | Johnson et al. |
| 2011/0315237 A1* | 12/2011 | Jenkins ................... A61M 1/16 137/312 |

(Continued)

FOREIGN PATENT DOCUMENTS

| DE | 10307896 | 9/2004 |
| EP | 0611228 | 8/1994 |
| WO | WO 2009/006471 | 1/2009 |

OTHER PUBLICATIONS

International Search Report and Written Opinion in International Appln. No. PCT/US2022/049495, dated Feb. 22, 2023, 12 pages.

Primary Examiner — Courtney B Fredrickson
(74) Attorney, Agent, or Firm — Fish & Richardson P.C.

(57) ABSTRACT

A leak detector is provided that is incorporated into the wheels of a moveable medical device and/or cart or cabinet therefor. By incorporating a leak detector into the wheels themselves of the movable medical device, the leak detector, despite movement of the medical device, is suitably located to locate leaks with respect to the medical device at all times and requires no additional setup. The leak detector can further be tested by and interface with the moveable medical device to ensure the leak detector is in working condition and provide a convenient interface for a user. Additionally, by using this technology on each of the multiple wheels of a moveable medical device, the detectable area may be bigger than a leak detector at only one location.

20 Claims, 8 Drawing Sheets

(56) References Cited

U.S. PATENT DOCUMENTS

| | | | |
|---|---|---|---|
| 2013/0184638 A1* | 7/2013 | Scarpaci | A61M 1/282 604/28 |
| 2015/0025449 A1* | 1/2015 | Yuds | G16Z 99/00 604/28 |
| 2022/0074099 A1* | 3/2022 | Woodham, Jr. | D06F 34/05 |

* cited by examiner

LEAK DETECTOR ON MOVABLE MEDICAL DEVICE

TECHNICAL FIELD

This application relates generally to systems and methods for a leak detector on a movable medical device, such as a dialysis machine.

BACKGROUND

Medical devices, such as dialysis machines, are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate, or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance. Both HD and PD machines may include displays with touch screens or other user interfaces that display information of a dialysis treatment and/or enable an operator or patient to interact with the machine.

Dialysis involves moving fluids: blood, dialysate, effluent, and, depending on the system, water. The fluids are pumped to interact with the patient and then they are drained when their work is complete. This fluid can be piped in through a tap, stored in jugs or bags, or move through tubing. Dialysis takes place in hospitals, clinics, homes, and, in its simplest form of continuous ambulatory peritoneal dialysis (CAPD), any controlled space that is away from random sources of infection.

There exists potential for ruptured tubing, improper connections, and faulty components in dialysis machines and systems and other devices or systems used in conjunction, like a reverse osmosis (RO) system, that may cause fluid leaks. Additionally, improperly connected dialysate tubing to the dialyzer, mis-routed drain tubing, cross-threaded or loose tubing connections, and punctured PD solution bags all have the potential to cause leaks. Leaks can cause costly damage to the facility or patient's home, create slip hazards, and, in the case of unnoticed blood leaks, can be fatal.

Devices exist on the market to detect certain types of leaks, including devices to blood leaks at a patient's access site or devices disposed under the dialysis machine or related system to detect leaks when a fluid conducts an electric current between a positive and negative wire terminal. Many leak devices use the same electrical conduction sensor for leaks, but they always require periodic battery replacement—for if the sensor lacks power, it cannot function. Moreover, these sensors also usually cover a very narrow area and require the user to guess the likeliest path a spill may take to reach the sensor or determine where the most likely spot the leak will pool. These problems may be compounded by the fact that dialysis machines have wheels and may be moveable, and the user may wish to reposition the device but may forget about moving the leak detector or, if multiple leak detectors exist, become confused about which one is alarming and where. Furthermore, certain types of electromagnetic frequencies may also interfere with wireless leak detector signals.

Accordingly, it would be desirable to provide a system that addresses the above-noted concerns and other issues.

SUMMARY

According to the system described herein, a medical system comprises a medical device that performs a medical treatment, at least one wheel assembly that enables mobility of the medical device, and a leak detector system coupled with the at least one wheel assembly. The leak detector system comprises at least two conductive contacts disposed such that the contacts are electrically connected when the at least one wheel assembly is exposed to an electrically conductive fluid to form a circuit that causes detection of a leak. The leak detector system further comprises a connection to an interface of the medical device, and upon detection of the leak, an alarm is displayed on the interface of the medical device.

According further to the system described herein, a leak detection system for a movable medical device comprises at least two conductive contacts disposed on at least on wheel assembly of the movable medical device. The contacts are electrically connected when the at least one wheel assembly is exposed to an electrically conductive fluid to form a circuit that causes detection of a leak. A processor is included that receives a signal indicating the detection of the leak. A connection is provided to an interface of the medical device, wherein, upon detection of the leak, the leak detection system causes an alarm to be displayed on the interface of the medical device.

According to various implementations of the system described herein, the at least two conductive contacts may be disposed on two wheels of the at least one wheel assembly. The least one wheel assembly may include a first wheel assembly and a second wheel assembly, and a first conductive contact of the at least two conductive contacts may be disposed on the first wheel assembly, and a second conductive contact of the at least two conductive contacts may be disposed on the second wheel assembly. The medical device may include a processor that is configured to perform an operational check on the leak detector system. The medical device may include a wireless transmitter that transmits the alarm to a remote device, and the remote device may be a mobile device of a patient and/or a device monitored by a remote server. The medical device may be a dialysis machine. The connection to the interface of the medical device may be a wired connection. Upon detecting the leak, the medical device may cause a pumping operation of the medical device to stop.

BRIEF DESCRIPTION OF THE DRAWINGS

Implementations and features of the system described herein are explained with reference to the several figures of the drawings, which are briefly described as follows.

DETAILED DESCRIPTION

Figure 1:
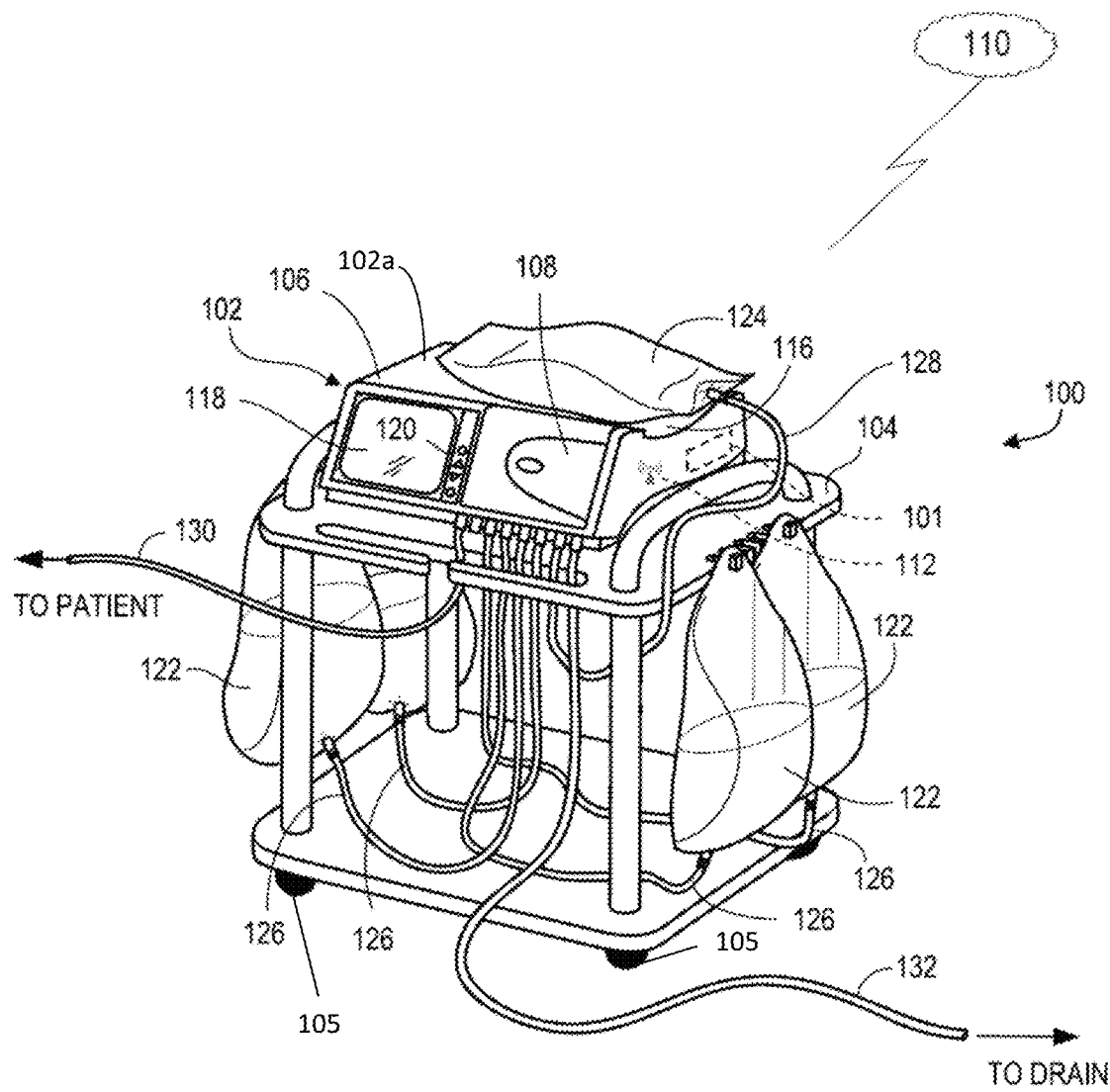
FIG. 1 illustrates an exemplary implementation of a dialysis machine in a dialysis system configured for use in accordance with the present disclosure.

FIG. 1 shows an example of a medical device system, implemented as a peritoneal dialysis (PD) system 100, that is configured for use in accordance with an exemplary implementation of the system described herein. In some implementations, the PD system 100 may be configured for use at a patient's home. The PD system 100 may include a dialysis machine 102 (e.g. a PD machine, also referred to as a PD cycler) which, in some implementations may be seated on a cabinet or cart 104 having one or more wheels 105 and be movable. The dialysis machine 102 may include a housing 106, a door 108, and a cartridge interface for contacting a disposable PD cassette, or cartridge, when the cartridge is disposed within a compartment formed between the cartridge interface and the closed door 108. A heater tray 116 may be positioned on top 102a of the housing 106. The heater tray 116 may be any size and shape to accommodate a bag of dialysate (e.g., a 5 L bag of dialysate). The dialysis machine 102 may also include a user interface such as a touch screen 118 and control panel 120 operable by a user (e.g., a caregiver or a patient) to allow, for example, set up, initiation, and/or termination of a PD treatment.

Dialysate bags 122 may be suspended from the sides of the cart 104, and a heater bag 124 may be positioned in the heater tray 116. Hanging the dialysate bags 122 may improve air management as any air is disposed by gravity to a top portion of the dialysate bag 122. Valves may be attached to a bottom portion of the dialysate bags 122 so fluid is drawn out and air delivery is minimized. Dialysate from the dialysate bags 122 may be transferred to the heater bag 124 in batches. For example, a batch of dialysate may be transferred from the dialysate bags 122 to the heater bag 124, where the dialysate is heated by the heating element. When the batch of dialysate has reached a predetermined temperature (e.g., approximately 98°–100° F., 37° C.), the batch of dialysate may be flowed into the patient. The dialysate bags 122 and the heater bag 124 may be connected to the cartridge via dialysate bag lines 126 and a heater bag line 128, respectively. The dialysate bag lines 126 may be used to pass dialysate from dialysate bags 122 to the cartridge during use, and the heater bag line 128 may be used to pass dialysate back and forth between the cartridge and the heater bag 124 during use. In addition, a patient line 130 and a drain line 132 may be connected to the cartridge. The patient line 130 may be connected to a patient's abdomen via a catheter and may be used to pass dialysate back and forth between the cartridge and the patient's peritoneal cavity during use. The drain line 132 may be connected to a drain or drain receptacle and may be used to pass dialysate from the cartridge to the drain or drain receptacle during use.

The touch screen 118 and the control panel 120 may allow a user to input various treatment parameters to the dialysis machine 102 and to otherwise control the dialysis machine 102. In addition, the touch screen 118 may serve as a display. The touch screen 118 may function to provide information to the patient and the operator of the PD system 100. For example, the touch screen 118 may display information related to a dialysis treatment to be applied to the patient, including information related to a prescription. In various embodiments, the control panel 120 may also include audio and video component capabilities, including speakers, microphones and/or cameras.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., temperature and pressure sensors, and control the dialysis machine 102 based on the received data. For example, the processing module 101 may adjust the operating parameters of the dialysis machine 102.

The dialysis machine 102 may be configured to connect to a network 110. The connection to network 110 may be via a wireless connection, such as via WiFi or Bluetooth, or in some cases a non-wireless connection, as further discussed elsewhere herein. The dialysis machine 102 may include a connection component 112 configured to facilitate the connection to the network 110. The connection component 112 may be a transceiver for wireless connections and/or other signal processor for processing signals transmitted and received over a wired connection. In the case of a wired connection, the connection component 112 may be a port enabling a physical connection to a network component. Other medical devices (e.g., other dialysis machines) or components may be configured to connect to the network 110 and communicate with the dialysis machine 102.

Although discussed herein principally in connection with a peritoneal dialysis machine, the system described herein may be used and implemented in connection with other types of medical devices having one or more displays, including hemodialysis machines both in the clinic and at home and/or other medical devices.

Figure 2:
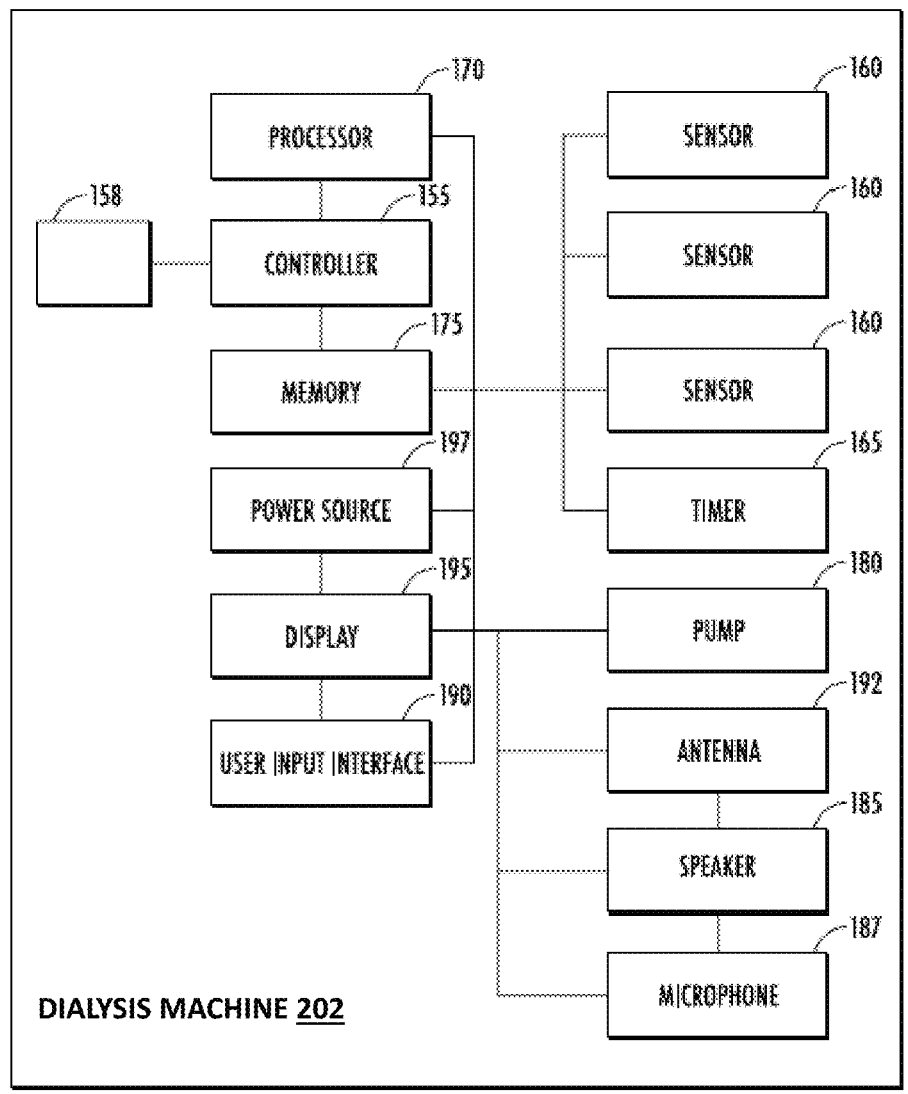
FIG. 2 is a schematic illustration of an exemplary embodiment of the dialysis machine that is configured for use in accordance with the present disclosure.

FIG. 2 is a schematic illustration of an exemplary embodiment of a dialysis machine 202 that may, for example, be an implementation of the dialysis machine 102, and that is configured for use in accordance with the present disclosure. The machine 202 may be a home dialysis machine for performing a dialysis treatment on a patient and may be implemented in the system 100 described above. As further noted elsewhere herein, although discussed principally in connection with a peritoneal dialysis machine, the dialysis machine 202, and the principles and techniques of the system described herein, may be used and implemented in connection with other types of medical devices, including home hemodialysis machines and/or other home medical devices. A controller 155, that may be a component of the processing module 101, may automatically control execution of a treatment function during a course of dialysis treatment. The controller 155 may be operatively connected to the sensors 160 and deliver a signal to execute a treatment function or a course of treatment associated with various treatment systems. In some embodiments, a timer 165 may be included for timing triggering of the sensors 160.

In some embodiments, the machine 202 may also include a processor 170, and memory 175, the controller 155, the processor 170, and/or the memory 175, or combinations thereof, that may separately or collectively part of the processing module 101, that may receive signals from the sensor(s) 160 indicating various parameters. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pumps and/or compressors to deliver dialysate and the like) and a status associated with specific operations (e.g., ready to execute, executing, completed, successfully completed, queued for execution, waiting for control signal, and the like).

In some embodiments, the dialysis machine 202 may include at least one pump 180 operatively connected to the controller 155. During a treatment operation, the controller 155 may control the pump 180 for pumping fluid, e.g., fresh and spent dialysate, to and from a patient. For example, the pump 180 may transfer dialysate from the dialysate bag 122 through, for example, a cassette insertable into a port formed in the dialysis machine, to the heating chamber 152 prior to transferring the dialysis to the patient. In an embodiment, the pump 180 may be a peristaltic pump. The controller 155 may also be operatively connected to a speaker 185 and a microphone 187 disposed in the machine 202. A user input interface 190 may include a combination of hardware and software components that allow the controller 155 to communicate with an external entity, such as a patient, caregiver or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The machine 202 may also be wirelessly connectable via an antenna 192 for remote communication that may be a part of the connection component 112. The machine 202 may also include a display 195 and a power source 197.

The sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 202. These platform services may include inter-process and network communication, file system management and standard database manipulation. One or more of many operating systems may be used, and examples are not limited to any particular operating system or operating system characteristic.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 202, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 202 or may be coupled to the machine 202 via a communication port or wireless communication links, shown schematically as communication element 158 that may be a part of the connection component 112. According to various examples, the communication element 158 may support a variety of one or more standards and protocols, examples of which include wireless and/or non-wireless communication, such as USB, Wi-Fi, TCP/IP, Ethernet, Bluetooth, among others. As a component disposed within the machine 202, the controller 155 may be operatively connected to any of the sensors 160, the pump 180, and the like. The controller 155 may communicate control signals or triggering voltages to the components of the machine 202. As discussed, exemplary embodiments of the controller 155 may include wireless communication interfaces. The controller 155 may detect remote devices to determine if any remote sensors are available to augment any sensor data being used to evaluate the patient.

Figure 3:
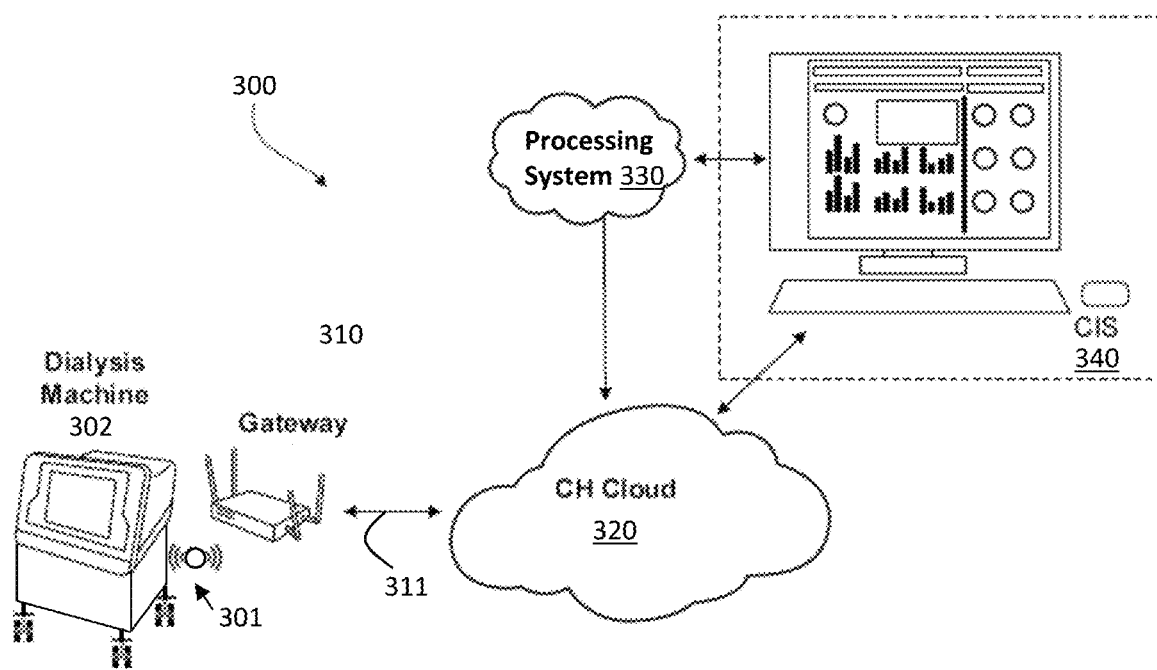
FIG. 3 is a schematic illustration showing an example of a connected health (CH) system that may include, among other things, a processing system, a CH cloud, and a gateway device that may be used in connection with the system described herein.

FIG. 3 is a schematic illustration showing an example of a connected health (CH) system 300 that may include, among other things, a gateway device 310 and a CH cloud service 320. The CH system 300 may provide for communication and/or connectivity of a dialysis machine 302, that may be similar to one or more of the dialysis machines discussed elsewhere herein, such as the dialysis machines 102, 202, and/or may include a different type of dialysis machine, such as a home HD machine. Via the CH system 300, the dialysis machine 302 may be connected to internal and external networks, including with remote servers and/or entities. The gateway device 310 may serve as a communication device facilitating communication among components of the CH system 300. The CH cloud 320 may be a cloud-based application or service (e.g. Software as a Service) implementation that serves as a communication pipeline that facilitates the transfer of data among components of the CH system 300 via connections to a network such as the Internet. A processing system 330 may be a server and/or cloud-based system that processes, compatibility checks and/or formats medical information, including prescription information generated at a clinical information system (CIS) 340 of a clinic or hospital, in connection with data transmission operations of the CH system 300. The CH system 300 may include appropriate encryption and data security mechanisms.

In various embodiments, the gateway device 310 is in communication with the dialysis machine 302 via a wireless connection 301, which may be done over a short range network, such as Bluetooth, Wi-Fi and/or other appropriate type of local or short range wireless connection. The gateway 310 may also be in connection with the CH cloud 310 via an external network (e.g. the Internet) connection 311. The gateway device 310 is configured to transmit/receive data to/from the CH cloud 320 and transmit/receive data to/from the dialysis machine 302. In various implementations, the dialysis machine 302 may poll the CH cloud 320 for available files (e.g., via the gateway device 310), and the dialysis machine 302 may temporarily store available files for processing.

According to implementations of the system described herein, a leak detector system incorporated into the wheels of a moveable medical device, such as a dialysis machine (and/or cart or cabinet thereof) is provided. Such a system may address issues of separate leak detectors that may often need to have their batteries periodically replaced, can get lost or damaged and rendered ineffective, or simply are in the wrong place at the wrong time and cannot sense a dialysis-associated leak. By incorporating a leak detector into the wheels themselves of the movable medical device, the leak detector, despite movement of the medical device, is suitably located to locate leaks with respect to the medical device at all times and requires no additional setup. The leak detector can further be tested by and interface with the mobile medical device to ensure the leak detector is in working condition and provide a convenient interface for a user. Additionally, by using this technology on each of the multiple wheels of a moveable medical device, the detectable area may be bigger than a leak detector at only one location.

Figure 4A:
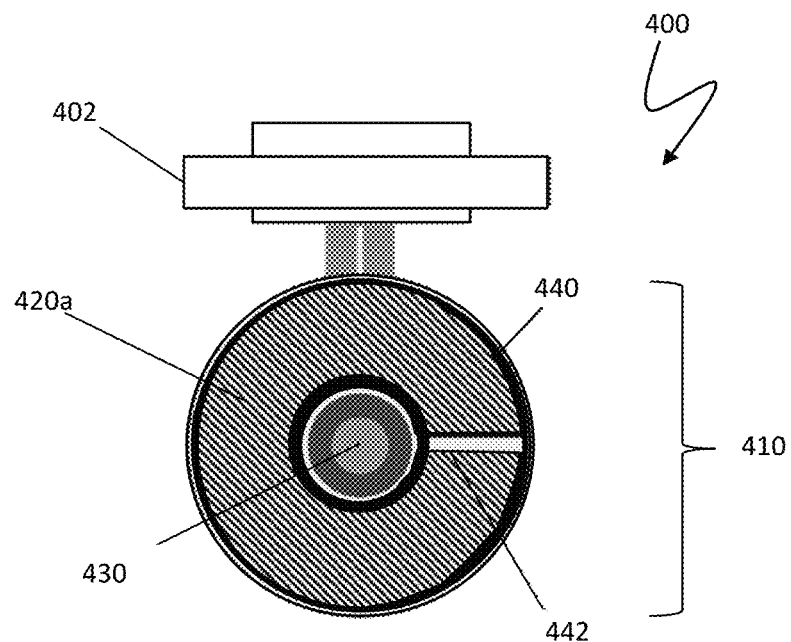
FIGS. 4A and 4B are schematic illustrations showing a leak detector system according to the system described herein that is integrated into the one or more wheel of a movable medical device, such as a dialysis machine.

FIG. 4A is a schematic illustration 400 showing a leak detection system 410 (that may also interchangeably be referred to herein as a leak detector) according to the system described herein that is integrated into the one or more wheel 420 of a movable medical device, such as a dialysis machine 402 (or a cabinet or cart therefor, and which may be collectively referred to in the description herein as the mobile medical device or dialysis machine, understanding that a movable medical device or dialysis machine may be positioned on a cart and/or may be incorporated into a movable cabinet structure). The leak detector 410 may be wired directly into the user interface of the dialysis machine 402. This allows the leak detector 410 to travel with the dialysis machine 402 and allows a user interface of the leak detector 410 to be accessible by the user of the dialysis machine 402. In an implementation, a conductive (e.g. metal) ring 440 near or on the edge of the wheel 420*a,* that may be a wheel of an insulated caster-type wheel assembly 420, is electrically connected to a hub 430 of the wheel 420*a* via a conductive (e.g. metal) link 442. The conductive link 442 makes contact with an electrically conductive caged bearing 450 (see FIG. 4B) to facilitate transfer of the electrical signal to wires in the cabinet of the dialysis machine 402. The electrically conductive portion of the wheel 420 does not need to be limited to a ring on the wheel, but in other implementations may include a coating on the wheel 420 or the wheel 420 itself could be made of metal or other conductive material.

Figure 4B:
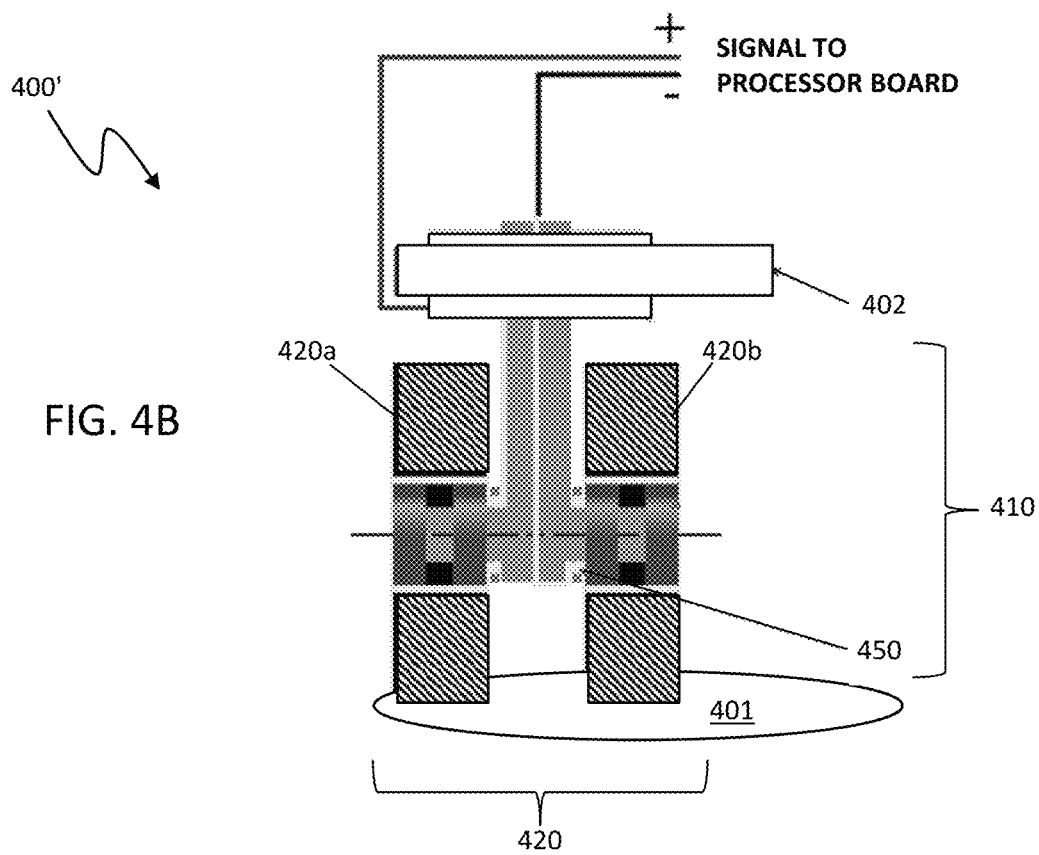

FIG. 4B is a schematic illustration 400' showing another view of the implementation of the leak detector 410 according to the system described herein. The wire circuit of the leak detector 410 passes from the wheel 420*a* through a power supply and to a processor board and back to the other wheel 420*b* of the caster assembly 420. In some implementations the processor board may be a processor board of the dialysis machine 402 (see, e.g., the processor and other components of FIG. 2). In other implementations, the processor board may be considered as a processor component of the leak detection system that may be located on the processor board of the dialysis machine and/or may be a processor located separately from the processor board of the dialysis machine 402. When an electrically conductive liquid (like blood or dialysate) from a leak 401 completes the circuit between the two wheels 420*a,b* of the caster 420, the dialysis machine 402 registers the signal as a detected leak and alarms, displaying a notification on a display screen of the dialysis machine 402 (see, e.g., the touch screen 118 of the dialysis machine 102). The alert message may also be transmitted wirelessly to other devices like a smartwatch, smartphone, tablet, etc., to notify the operator, as further discussed elsewhere herein. The metal ring 440 on the insulated wheels 420*a,b* would not make direct contact with the floor to prevent false alarms when resting on or rolling over an electrically conductive surface (e.g., an elevator threshold). Periodic safety checks can be performed in the circuit, but the advantage is that no setup is required and the sensors use the dialysis machine's power supply without cumbersome wires outside of the dialysis machine.

Figure 5A:
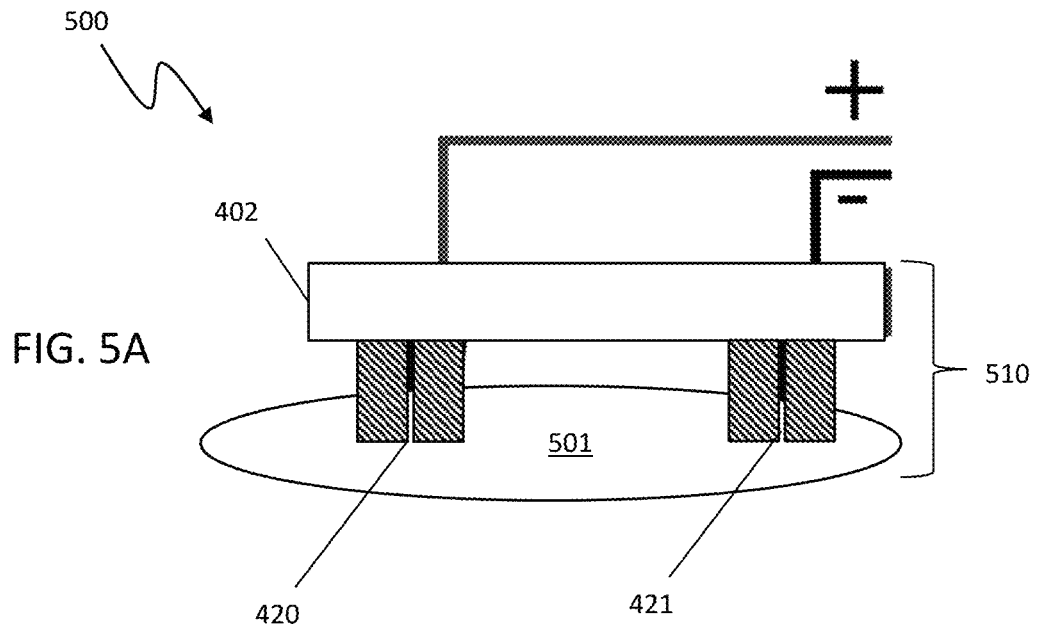
FIGS. 5A and 5B are schematic illustrations of other implementations of a leak detector system according to the system described herein.
Figure 5B:
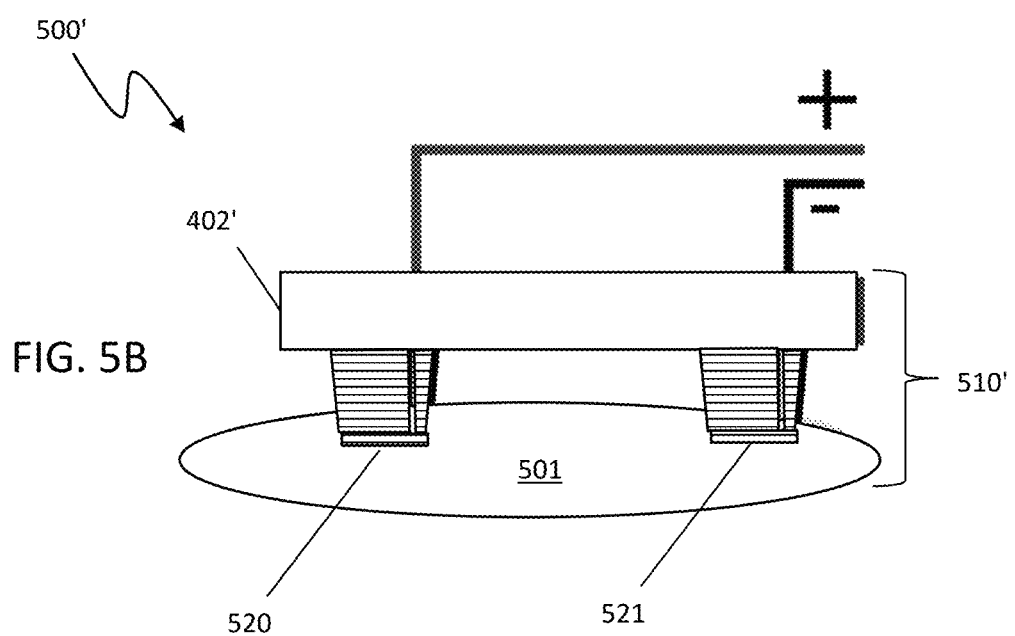

FIG. 5A is a schematic illustration 500 of another implementation of a leak detection system 510 in which each set of wheels 420, 421 (or forked caster) carries a unique charge and the dialysis machine 402 would detect a difference when an electrically conductive liquid of a leak 501 touches more than one set of wheels 520, 521. This would mean a larger spill is necessary for detection. It is further noted that, in another embodiment, the method of the system described herein may work for a smaller portable medical device, without movable wheels. Instead, each foot would carry a charge. FIG. 5B is a schematic illustration 500' showing a dialysis machine 402' with insulated feet 520, 521 so it could be placed on a conductive surface (e.g., metal tabletop) without causing false leak alarms. Surface tension in the liquid leak would allow the fluid to climb high enough above the very bottom of the insulated feet 520, 521 to a conductive ring to complete the circuit between the feet 520, 521 and cause the dialysis machine 402' to detect a leak. Each of the feet 520, 521 may be vertically split into two different charges for improved coverage in a narrower area. In another implementation, the feet 520, 521 may be wheels with a wheel lock, such that a leak detecting circuit of a leak detector 510' (having features and functions like the leak detector 510 for this implementation) on a foot 520, 521 may descends to rest on the floor below the dialysis machine 402' when the wheel lock is engaged. A switch at the wheel lock may signals it has been pressed against the floor.

Figure 6:
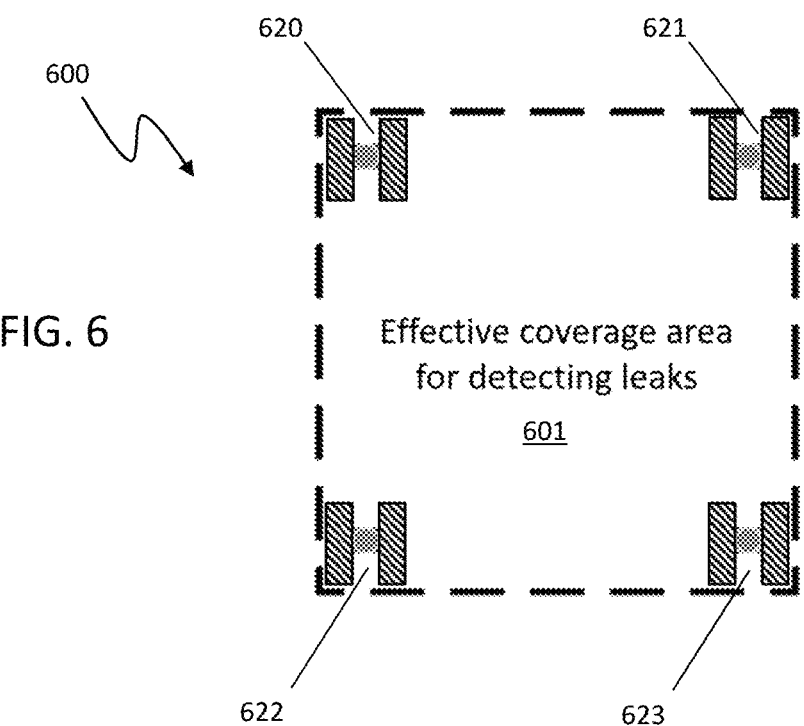
FIG. 6 is a schematic illustration showing the effective coverage area for a leak detection system according to the system described herein incorporated into four wheel assemblies.

FIG. 6 is a schematic illustration 600 showing the effective coverage area 601 for a leak detection system according to the system described herein incorporated into four wheel assemblies 620, 621, 622, 623. The coverage area 601 may be advantageously larger than for a single leak detector.

Figure 7:
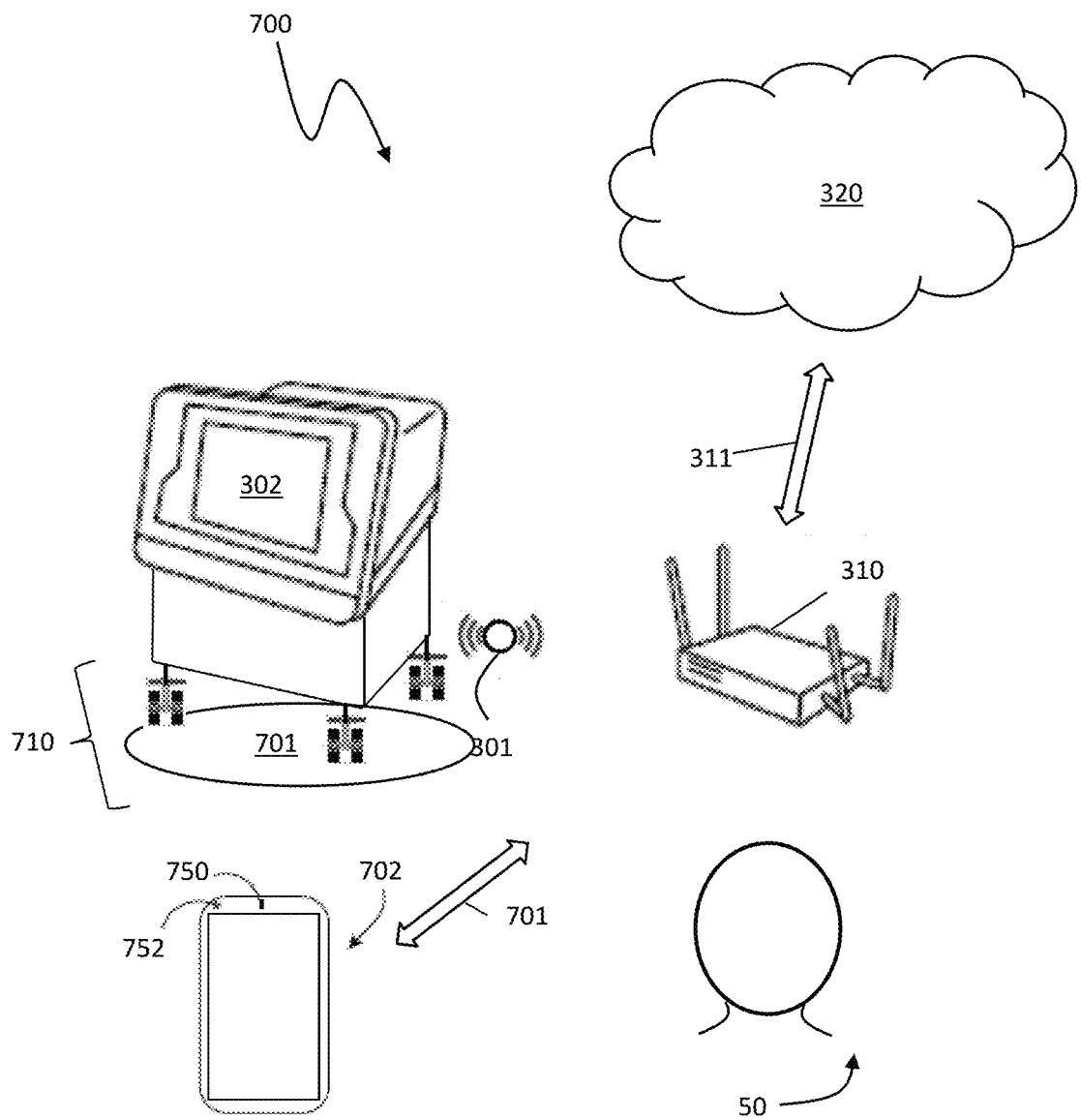
FIG. 7 is a schematic illustration showing an example of a system that includes components of the connected health system, including the dialysis machine and the gateway device in communication with a cloud service, and used in connection with a leak detector according to the system described herein.

FIG. 7 is a schematic illustration showing an example of a system 700 that includes components of the connected health system 300 described above, including the dialysis machine 302 and the gateway device 310 in communication with a cloud service 320, and used in connection with a leak detector according to the system described herein. A mobile computing device 702 of a patient 50 may be in communication (e.g., wired or wireless communication) 701 with one or more of the dialysis machine 302, the gateway device 310, and the cloud service 320. In the illustrated example, the mobile computing device 702 is a mobile phone or smartphone, but other mobile computing devices may also or alternatively be used, such tablet computers, laptop computers, etc. The mobile computing device 702 includes a microphone 750 and a speaker 752 and may be configured to provide voice interface capability as well as display and touch screen interfacing. The mobile computing device 702 may serve as a communication conduit between the dialysis machine 302 and the CH cloud 320, or between the dialysis machine 302, the gateway device 310, and/or the CH cloud 320.

A leak detection system 710 having features and functions as discussed above (e.g. like the leak detection system 410) may be incorporated into the dialysis machine 302 and/or cart or cabinet on which the dialysis machine 302 is positioned. When an electrically conductive liquid (like blood or dialysate) from a leak 701 completes the circuit between one or more wheels or caster assemblies, the dialysis machine 302 registers the signal as a detected leak and alarms, displaying a notification on a display screen of the dialysis machine 302. The alert message may also be transmitted wirelessly via the connected health system 300, including to the mobile computing device 702 and/or via the gateway device 310 to the cloud service 320. The alert may thereby be remotely monitored by either or both of the mobile computing device 702 and/or a system in communication with the cloud service 320, such as a clinical information system (e.g. the CIS 340). Appropriate responsive action may then be initiated, including by remote contact options to contact the patient 50 and/or causing a pumping or other functioning operation of the medical device to stop.

Figure 8:
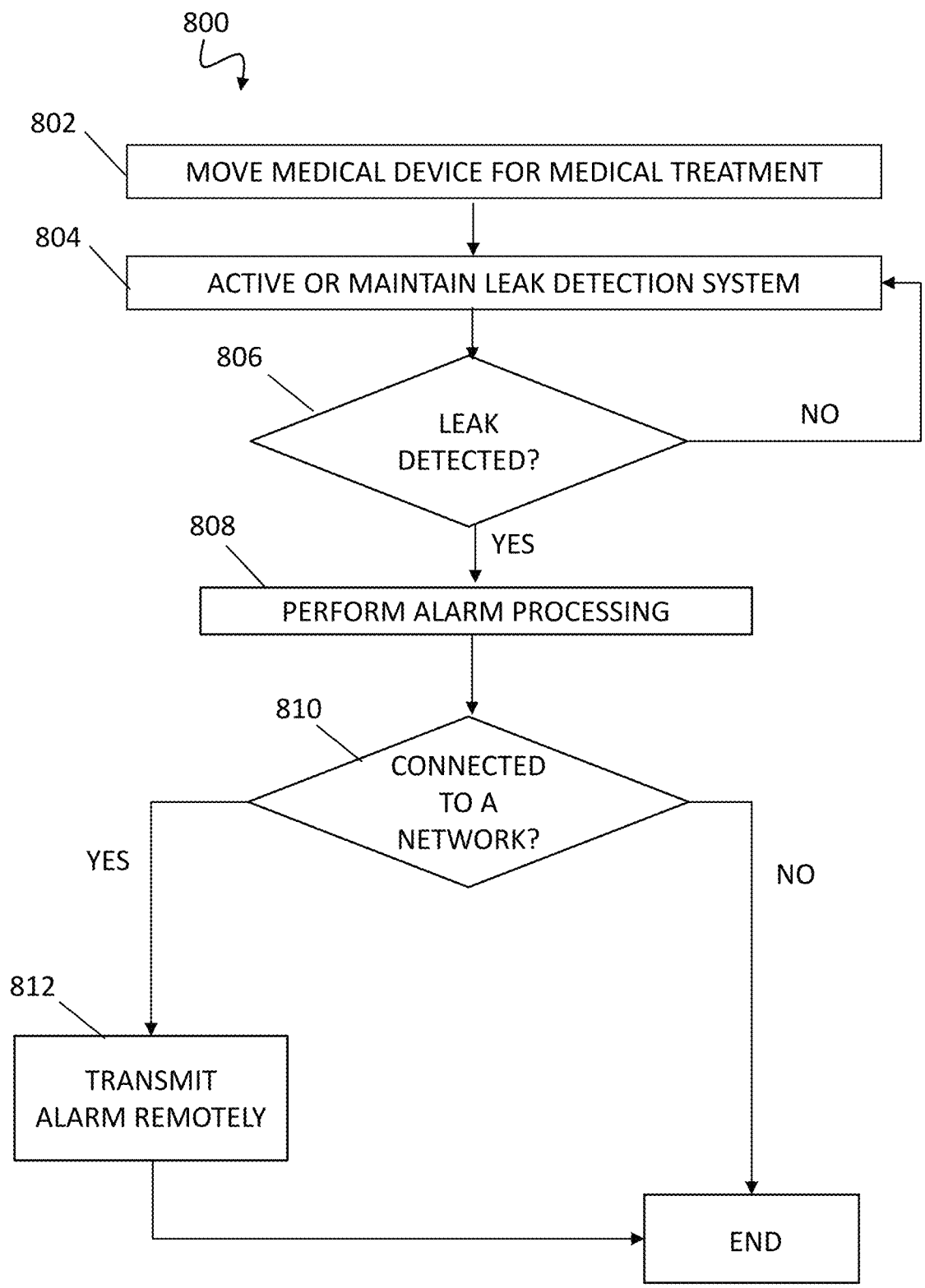
FIG. 8 is a flow diagram showing flow processing for an iteration of leak detection according to an implementation of the system described herein.

FIG. 8 is a flow diagram 800 showing flow processing for an iteration of leak detection according to an implementation of the system described herein. At a step 802, a movable medical device is moved into a position to provide a medical treatment, such as a dialysis treatment. At a step 804, a leak detection system as described herein that is incorporated into the movable medical device, for example, into the wheels thereof, is activated or maintained for monitoring for leaks. The activation may be either automatic or controlled via an interface of the medical device. At a decision step 806, it is determined whether a leak has been detected by the activated leak detection system, which may be determined by a processor board of the medical device that is electrically connected to the leak detection system. If NO at decision step 806 then processing reiterates back to the step 804. If YES at decision step 806, then processing proceeds to a step 808 where an alarm is generated concerning the leak detection, and alarm processing is performed including displaying the alarm on a display screen of the movable medical device and/or other alarm processing including causing an operation of the medical device to stop. At a decision step 810, it is determined whether the medical device is connected via a network of a connected health system, such as either a local network or a remote network, e.g. via a gateway device. If NO at the decision step 810 then processing is concluded for this described iteration of the leak detection processing. If YES at the decision step 810 then processing proceeds to a step 812 where the leak alarm is transmitted remotely, such as via a local network to a patient's smartphone or other connected device and/or to a remote location via a cloud service using a gateway device.

Embodiments or implementations discussed herein may be combined with each other in appropriate combinations in connection with the system described herein. Additionally, in some instances, the order of steps in the flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions. Data exchange and/or signal transmissions to, from and between components of the system may be performed using wired or wireless communication. This communication may include use of one or more transmitter or receiver components that securely exchange information via a network, such as the Internet, and may include use of components of local area networks (LANs) or other smaller scale networks, such as Wi-Fi, Bluetooth or other short range transmission protocols, and/or components of wide area networks (WANs) or other larger scale networks, such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or

What is claimed is:

1. A medical system, comprising:
   a medical device that is configured to perform a medical treatment;
   at least one wheel assembly that enables mobility of the medical device;
   a leak detector system coupled with the at least one wheel assembly;
   wherein the leak detector system comprises:
      at least two conductive contacts disposed on the at least one wheel assembly such that the contacts are electrically connected when the at least one wheel assembly is exposed to an electrically conductive fluid to form a circuit that causes detection of a leak; and
      a connection to an interface of the medical device, wherein, upon detection of the leak, an alarm is configured to be displayed on the interface of the medical device.

2. The medical system according to claim 1, wherein the at least two conductive contacts are disposed on two wheels of the at least one wheel assembly.

3. The medical system according to claim 1, wherein the least one wheel assembly includes a first wheel assembly and a second wheel assembly, and wherein a first conductive contact of the at least two conductive contacts is disposed on the first wheel assembly and a second conductive contact of the at least two conductive contacts is disposed on the second wheel assembly.

4. The medical system according to claim 1, wherein the medical device includes a processor that is configured to perform an operational check on the leak detector system.

5. The medical system according to claim 1, wherein the medical device includes a wireless transmitter that is configured to transmit the alarm to a remote device.

6. The medical system according to claim 5, wherein the remote device is a mobile device of a patient.

7. The medical system according to claim 5, wherein the remote device is a device monitored by a remote server.

8. The medical system according to claim 1, wherein the medical device is a dialysis machine.

9. The medical system according to claim 1, wherein the connection to the interface of the medical device is a wired connection.

10. The medical system according to claim 1, wherein, upon detecting the leak, the medical device is configured to cause a pumping operation of the medical device to stop.

11. A leak detection system for a medical device, comprising:
    at least one wheel assembly that enables mobility of the medical device;
    at least two conductive contacts disposed on the at least one wheel assembly, wherein the contacts are electrically connected when the at least one wheel assembly is exposed to an electrically conductive fluid to form a circuit that causes detection of a leak;
    a processor that receives a signal indicating the detection of the leak; and
    a connection to an interface of the medical device, wherein, upon detection of the leak, the leak detection system is configured to cause an alarm to be displayed on the interface of the medical device.

12. The leak detection system according to claim 11, wherein the at least two conductive contacts are disposed on two wheels of the at least one wheel assembly.

13. The leak detection system according to claim 11, wherein the least one wheel assembly includes a first wheel assembly and a second wheel assembly, and wherein a first conductive contact of the at least two conductive contacts is disposed on the first wheel assembly and a second conductive contact of the at least two conductive contacts is disposed on the second wheel assembly.

14. The leak detection system according to claim 11, wherein the processor is configured to perform an operational check on the leak detection system.

15. The leak detection system according to claim 11, further comprising a wireless transmitter that is configured to transmit the alarm to a remote device.

16. The leak detection system according to claim 15, wherein the remote device is a mobile device of a patient.

17. The leak detection system according to claim 15, wherein the remote device is a device monitored by a remote server.

18. The leak detection system according to claim 11, wherein the medical device is a dialysis machine.

19. The leak detection system according to claim 11, wherein the connection to the interface of the medical device is a wired connection.

20. The leak detection system according to claim 11, wherein, upon detecting the leak, the processor is configured to cause a pumping operation of the medical device to stop.

* * * * *